(12) United States Patent
Roine et al.

(10) Patent No.: US 9,588,021 B2
(45) Date of Patent: Mar. 7, 2017

(54) METHOD FOR DETERMINING CONDITION OF PIPING AND A SEQUENCE CONTROLLED SAMPLE PUMP

(75) Inventors: Johannes Roine, VTT (FI); Leif Kåll, VTT (FI); Olli Antson, VTT (FI)

(73) Assignee: Teknologian Tutkimuskeskus VTT Oy (FI)

( * ) Notice: Subject to any disclaimer, the term of this patent is extended or adjusted under 35 U.S.C. 154(b) by 494 days.

(21) Appl. No.: 14/111,182

(22) PCT Filed: Apr. 5, 2012

(86) PCT No.: PCT/FI2012/050346
§ 371 (c)(1),
(2), (4) Date: Nov. 1, 2013

(87) PCT Pub. No.: WO2012/140319
PCT Pub. Date: Oct. 18, 2012

(65) Prior Publication Data
US 2014/0053663 A1     Feb. 27, 2014

(30) Foreign Application Priority Data
Apr. 11, 2011  (FI) ..................... 20115342

(51) Int. Cl.
G01N 1/14    (2006.01)
G01M 1/00    (2006.01)
F04B 43/02   (2006.01)
F04B 51/00   (2006.01)
G01N 1/24    (2006.01)
G01N 29/14   (2006.01)
G01N 29/22   (2006.01)
G01N 1/22    (2006.01)

(52) U.S. Cl.
CPC ............... *G01N 1/14* (2013.01); *F04B 43/02* (2013.01); *F04B 51/00* (2013.01); *G01M 1/00* (2013.01); *G01N 1/2214* (2013.01); *G01N 1/24* (2013.01); *G01N 29/14* (2013.01); *G01N 29/222* (2013.01); *G01N 1/2258* (2013.01); *G01N 2291/0258* (2013.01)

(58) Field of Classification Search
None
See application file for complete search history.

(56) References Cited

U.S. PATENT DOCUMENTS

| | | | |
|---|---|---|---|
| 3,733,899 A | 5/1973 | Auphan et al. | |
| 3,819,305 A | 6/1974 | Klochemann et al. | |
| 3,950,136 A * | 4/1976 | Bellinga | G01N 1/22 422/83 |
| 4,344,743 A | 8/1982 | Bessman et al. | |

(Continued)

FOREIGN PATENT DOCUMENTS

DE   3611662      10/1987
JP   2006/200524  8/2006

*Primary Examiner* — Paul West
*Assistant Examiner* — Mark A Shabman (57) ABSTRACT

The invention relates to a sampling apparatus and method. In the sampling method, a sample is led through a flowline (20) to a pump (5) and from there on to sampling means (12, 13). According to the invention, the pump (5) is formed of an actual pump (5) and magnetic valves (4, 6) located on either side of it, which are controlled in such a way that the pumping is pulse-like.

13 Claims, 6 Drawing Sheets

1. Valve control power
2. CO2 & Pressure and line amplifier
3. Control computer
4. ⎫
5. ⎬ Form pump
6. ⎭

12 & 13 = CO2 collection sorbents
15 = Outlet (56) References Cited

U.S. PATENT DOCUMENTS

| | | | | |
|---|---|---|---|---|
| 4,858,130 A * | 8/1989 | Widrow | ............ | E21B 43/26 |
| | | | | 166/250.09 |
| 5,200,894 A * | 4/1993 | McCoy | ............ | E21B 47/042 |
| | | | | 702/6 |
| 6,244,100 B1 * | 6/2001 | Hastings | ............ | G01M 3/24 |
| | | | | 73/40.5 A |
| 6,757,218 B2 * | 6/2004 | Dubinsky | ............ | E21B 47/18 |
| | | | | 175/50 |

* cited by examiner

Fig. 1

1. Valve control power
2. CO2 & Pressure and line amplifier
3. Control computer
4.
5. } Form pump
6.

12 & 13 = CO2 collection sorbents
15 = Outlet

Fig. 5a
Fig. 5b
Fig. 5c ered the shape of the pressure pulse can be detected and
METHOD FOR DETERMINING CONDITION OF PIPING AND A SEQUENCE CONTROLLED SAMPLE PUMP The invention relates to a method according to Claim 1.

The invention also relates to a sequentially-controlled sampling pump.

The invention relates to continuously operating gas sampling.

The invention is particularly well suited to sampling taking place in connection with carbon-dioxide measurement.

Traditionally, the problem has required a separate so-called by-pass pump, and an actual sampling pump for a considerably smaller flow. Normal membrane pumps demand a relatively clean sample in order to operate reliably. Pumps according to the prior art also wear out quite quickly. So-called hose pumps change the flow when the shape of the hose changes, within a few weeks.

Traditional sampling pumps of a corresponding flow area require good pre-treatment of the sample.

One problem in the prior art is that the piping of the sampling arrangement may slowly become constricted and even blocked, and the constriction may have negative effects of the accuracy of the measurement. Sampling channels are particularly sensitive to constriction or blockage.

The present invention is intended to eliminate the aforementioned drawbacks of the prior art.

The invention is based on producing a pressure pulse in the piping and measuring the echo of the pressure pulse in the piping as a function of time. Particularly, the changes of the echoes created by the pressure pulse are assessed as a function of time.

One preferred embodiment of the invention is based on the system consisting of a membrane pump operating with the aid of a solenoid, magnetic valves controlling the flow, and a program, which times the operation of the pump and valves as desired.

The performance of the system is preferably monitored continuously by pressure and gas-content sensors, or by other state information sensors. The operating sequence of the system can be altered by using software, and it can be equipped with several different ways of recording a gas sample. The system can be connected to remote monitoring.

More specifically, the invention is characterized by what is stated in the characterizing portion of Claim 1.

The device according to the invention is, for its part, characterized by what is stated in the characterizing portion of Claim 10.

Considerable advantages are gained by means of the invention.

With the aid of the invention, gas samples can be collected from various gas flows over periods of even weeks or months, in such a way that the sampling remains stable and reliable. Thanks to remote monitoring, maintenance operations can be targeted sensibly on error situations, and the monitoring of the equipment by either the operator or, for example, public officials, is effective.

The invention is particularly suitable to continuous-operation gas sampling in the following conditions: a long and service-free operating time, a small transmission-time delay, dirtying particles possibly appearing in the gas, and, in addition, a wide dynamic as required of the device in sampling speed and controllability by an electric variable. The sampling pump now to be examined operates as both a by-pass pump and an actual sampling pump. In the present invention, the average flow remains constant from the sampling point to the solenoid pump, for the entire duration of the sampling period. The pump's outlet-side valve directs the gas to either the by-pass circulation, or, for example, to the sampling circulation after every $30^{th}$ operation. Thus, the operation can easily be varied at a large dynamic controlled by the control unit. The set of valves is considerably more immune to impurities than traditional equipment. A life of about $10^9$ operations is promised for the high-quality magnetic valves, which ensures very long service-free operation, even at an operating speed of 1000 operations an hour. Using the apparatus of the invention, it is possible to implement, for instance, $CO_2$ sampling from a flue-gas channel for use of the radio-carbon method. With the aid of the method, a plant can demonstrate the proportion of fossil and bio-origin $CO_2$ emissions in emissions trading, or in other mechanisms for restraining climate change.

The equipment is also suitable for the long-term sampling of other gases.

The pump to be examined produces pressure pulses of even quality, which produces quite high flow velocities momentarily in the piping. This blow-back principle is used to keep clean separately built traditional sampler-pipe networks. In this case, the principle is built into the method itself. The shape of the pressure pulse can be detected and can be used to determine the pump's operating capability and, for example, the remote reading of blockage in the gas inlet channel, the gas storage channel, or the gas outlet channel. The device according to the present invention is reliable and, with the aid of the sensoring connected to it, possible operating disturbances are detected immediately, so that breaks in operation will remain short.

In the following, the invention is examined with the aid of embodiments according to the accompanying figures.

Figure 1:
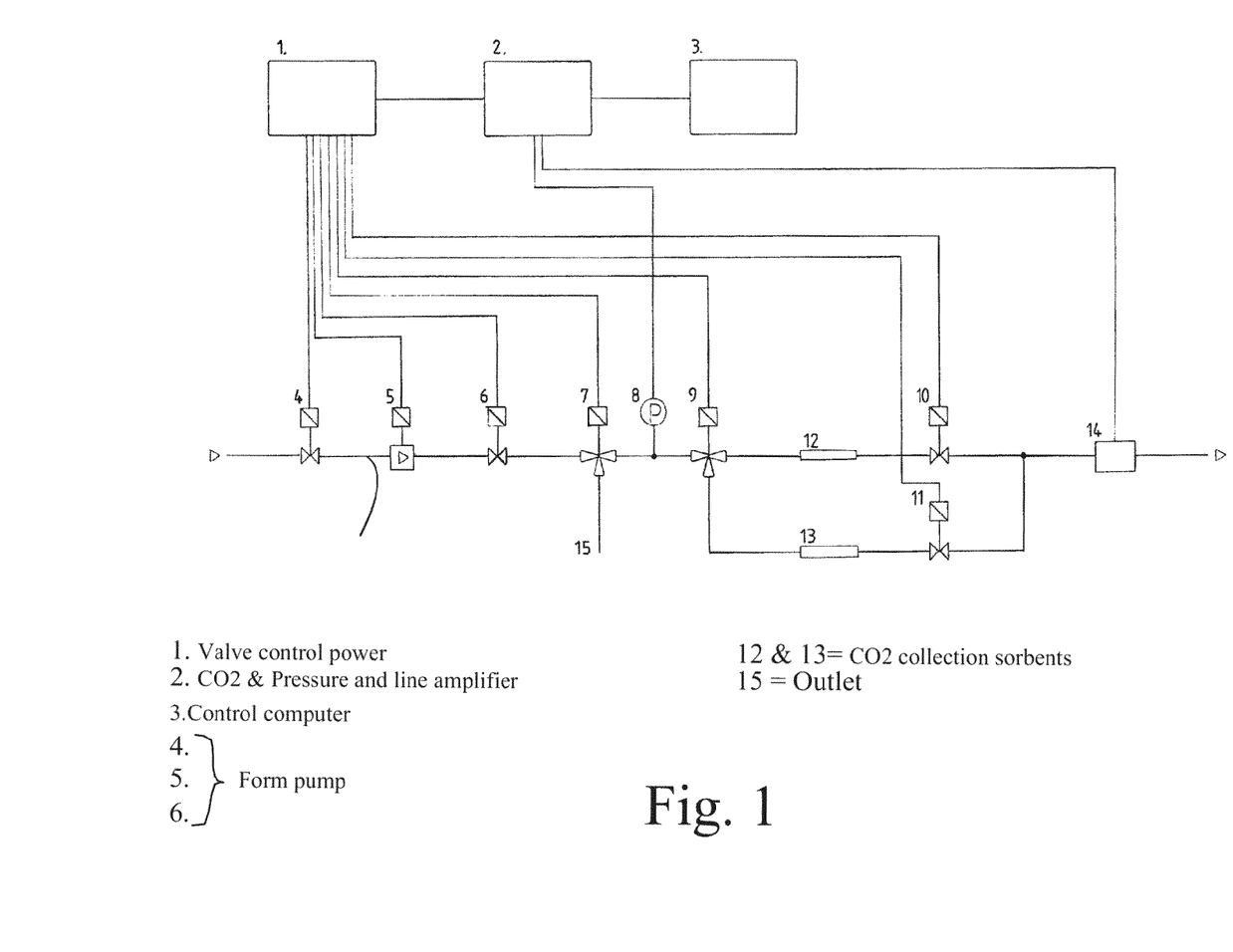
FIG. 1 shows one sampling apparatus according to the invention.

According to FIG. 1, the sampling system consists of a magnetic-valve body, which has been converted into a membrane pump. The magnetic valves 4 and 6, located on either side of the flowline 20 act as the valves of the pump 5. The outlet valves 7 and 9 divide the gas flow into different channels, e.g., the outlet channel 15 or the gas-sampling channels 12 and 13. The apparatus comprises a control unit 1 for controlling the valves and pump 5, a line amplifier 2 for measurement of the $CO_2$-measurement pressure, as well as a control computer 3 for controlling the elements 1 and 2. The pump control unit 1 also operates the magnetic valves 10 and 11 after the gas-sampling channel, which prevents contamination of the sample, for example, during periods when the plant is not operating and the sampler does not pump a sample. Operation can be controlled, for example, on the basis of the flow of gas, or by using a control signal corresponding to the plant's electrical power. Sampling can be easily regulated by altering the pumping frequency and the by-pass/sample ratio. The actual pump operation takes place in a range outside the piping's pneumatic resonances. The valves of a normal rotating membrane pump opens on the basis of the pressure difference of the gas being pumped. In that case, the shape and pressure of the piping connected to the pump significantly affect the output of the pump, the piping, as it is said, resonates. The pressure change of each work stage of a pump controlled by pulses is able to equalize before the start of the following operation. The operation then becomes highly immune to ambient disturbances. The outlet connection is shown by the reference number 15 and the pressure-measurement unit by the reference number 8. The pressure-measurement unit sees particularly the pressure pulses that arise from, for instance, the closing and opening of the valves 10, 11. This is the same phenomenon as in radar technology, in which echoes are analysed in order to perceive the surroundings. A pulse caused by the pump 5, and the valves 10 and 11 acts in the same way as an electric pulse. Each change in the impedance of the conductor network causes a back reflection, and this series of reflections is made visible by this single pressure-measurement unit, the pressure sensor 8. The delay of the reflections is directly proportional to the distance of the impedance change from the pressure sensor 8, i.e. the entire network around the pump 4, 5, 6 becomes visible to the pressure-measurement device.

Expressed mathematically:

$$L = \tfrac{1}{2} \cdot v \cdot T, \text{ in which}$$

L=the distance of the impedance-change point from the pressure sensor v=the propagation velocity of the pressure pulse in a gas or liquid T=the delay from the transmission of the pressure pulse to the reception of the reflection, the coefficient ½ takes into account the travel of the pressure pulse from the pump to the impedance change and back.

The static measurement of pressures according to the prior art does not produce a fraction of such an amount of observations.

Traditional sampling pumps for a corresponding flow area require good pre-treatment of the sample.

Figure 2:
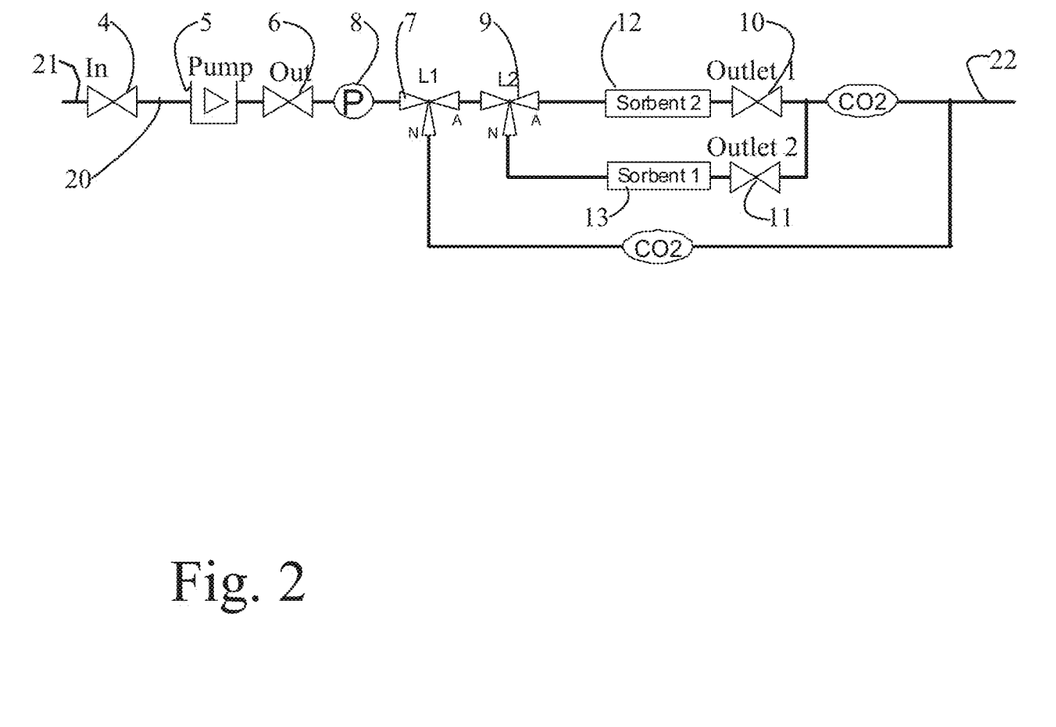
FIG. 2 shows a flow diagram of the device according to the invention.

FIG. 2 shows a flow diagram of the device according to the invention. It consists of simple shut-off valves 4, 6, 10, and 11 and two three-way valves 7 and 9. A modified shut-off valve 4, 5, and 6 acts as the pump. During each pumping period, the pressure is measured by a pressure meter 8, in order to monitor the operation of the device. The $CO_2$ values are measured, in order to ensure the operation of the pump. Possible filling with the sorbents 12 and 13 can be ascertained by means of a common $CO_2$ sensor on the sampling lines. In FIG. 2, the reference number 21 is used to show the inlet channel for gas (or liquid) to the measuring system and the reference number 22 the outlet channel for gas (or liquid) from the measuring system.

FIGS. 3-6 show the pressure-variation curves obtained in the sampling apparatus's pressure measurements, when the pump sucks gas from the flue-gas channel on the suction side and when the pump pumps the collected amount of gas towards the sorbent channel. There can be one or several sorbent channels; in FIGS. 3-6 there are two sorbents.

FIGS. 3a-6c also show 6 reading values, which are calculated from the measured pressure curves: the figures are obtained as the sum of the specific values of the difference of the broken-line curve 30 showing the initial situation of the sample collection and the solid-line curve 40 showing the moment of observation (the two uppermost figures relate to the left-hand suction-side curves, FIGS. 3a, 4a, 5a, 6a, the next two figures the upper right-hand 1$^{st}$ sorbent channel, FIGS. 3b, 4b, 5b, 6b, and the two lowest figures the lower right-hand 2$^{nd}$ sorbent channel, FIGS. 3c, 4c, 5c, 6,). The sorbent channel is represented by, for example, the elements 12 and 13 of FIG. 2 and the pressure measurement by element 8.

In practice it has been observed that, when the reading value formed with the aid of the curves of FIGS. 3a-6c exceeds the value 10, significant changes have occurred in the piping and measures may be, for example, the changing of sorbent 12 or 13 as a remote operation, or some other maintenance operation, depending on the part of the process in which the change has taken place (e.g., pressure flushing towards the flue-gas channel, if there is a blockage caused by particles on the suction side).

Figure 3A:
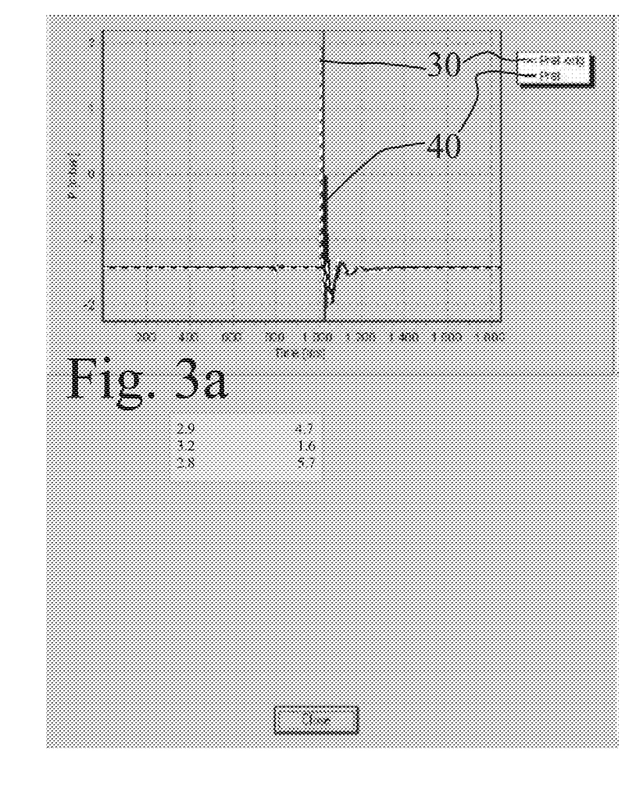
FIGS. 3a-3c show graphically the operation of the invention, in such a way that, in the left-hand FIG. 3a the suction channel is in normal operating condition. In the upper right-hand 3b, is the $1^{st}$ sorbent channel in normal operating condition, similarly in the lower right-hand is the $2^{nd}$ sorbent channel in normal operating condition. The reading values at the lower left hand depict the normal operating state.
Figure 3B:
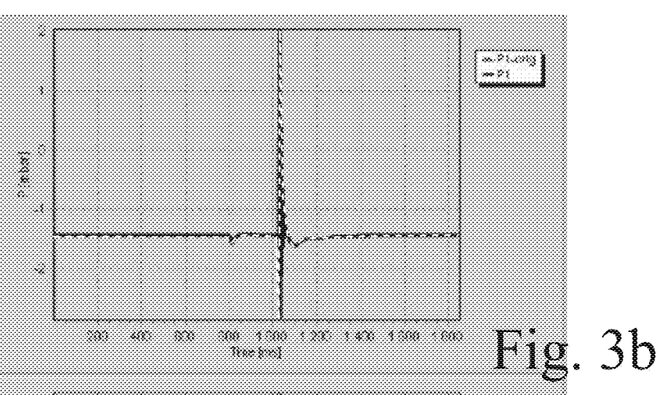
Figure 3C:
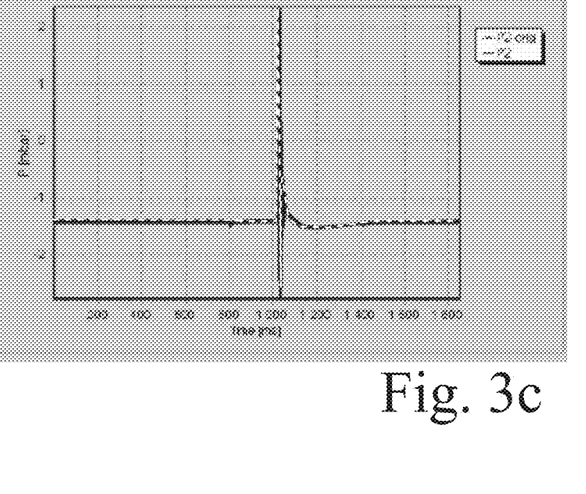

In FIG. 3a, the suction channel is in normal operating condition. According to the curves shown in Figure 3b, the 1$^{st}$ sorbent channel is in a normal operating condition, and similarly according to the curves shown in Figure 3c the 2$^{nd}$ sorbent channel is in normal operating condition. Thus, the curves 30 and 40 are more or less on top of each other. The reading values at the lower left depict a normal operating state, because the maximum value is 5.7.

Figures 4A, 4B, 4C:
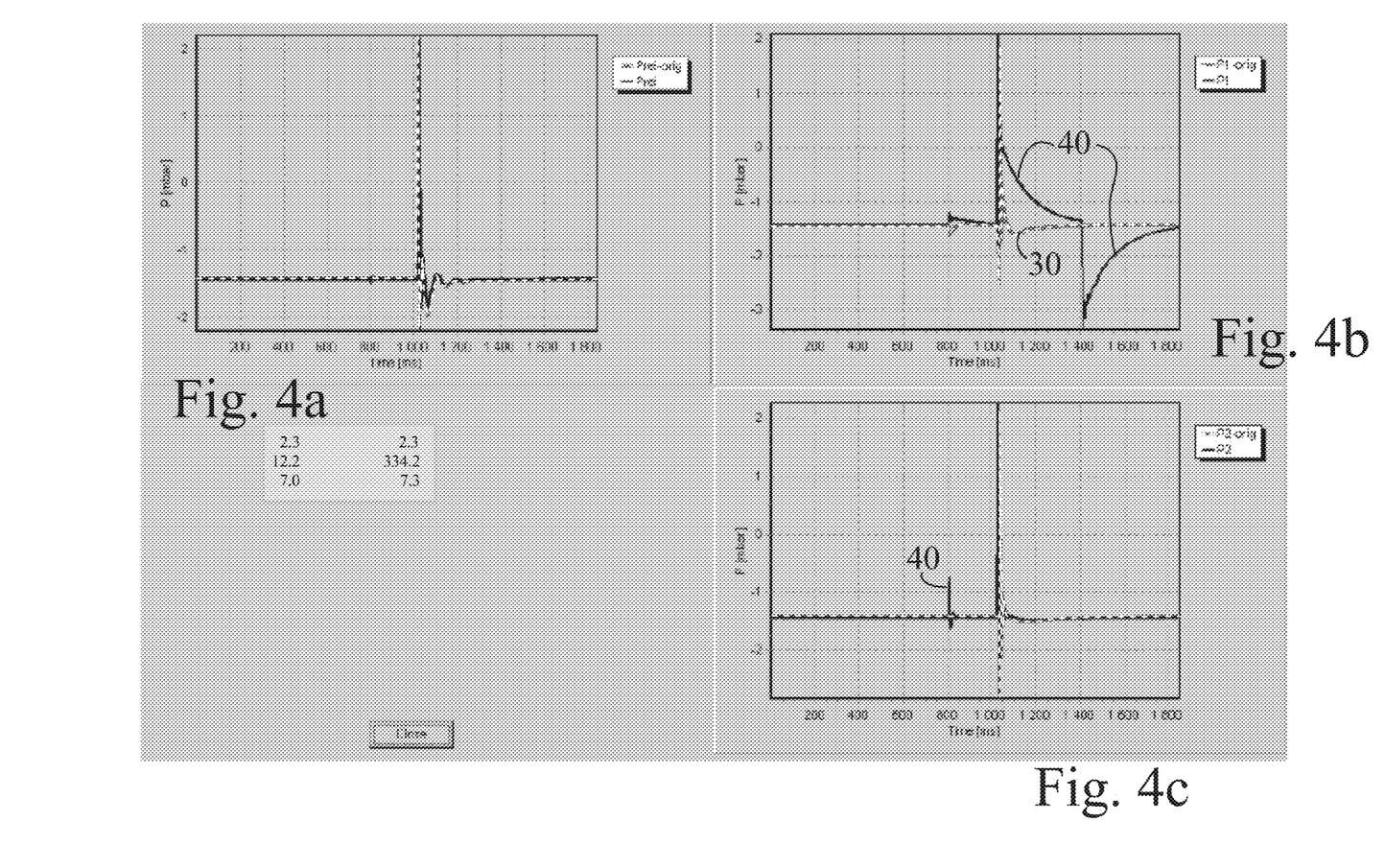
FIGS. 4a-4c show graphically the operation of the invention, in such a way that, in 4a the sorbent has been filled in the $1^{st}$ sorbent channel: a significant deviation in the pressure curve, as well as the reading values (12.2 and 334.2) indicate blockage of the sorbent channel in question.

According to FIG. 4b, sorbent has been filled in the 1$^{st}$ sorbent channel: a significant deviation can be seen in the pressure curve, similarly, the reading values (12.2 and 334.2) indicate a blockage in the sorbent channel in question. FIGS. 4a and 4c do not show that the limit values have been exceeded.

Figure 5A:
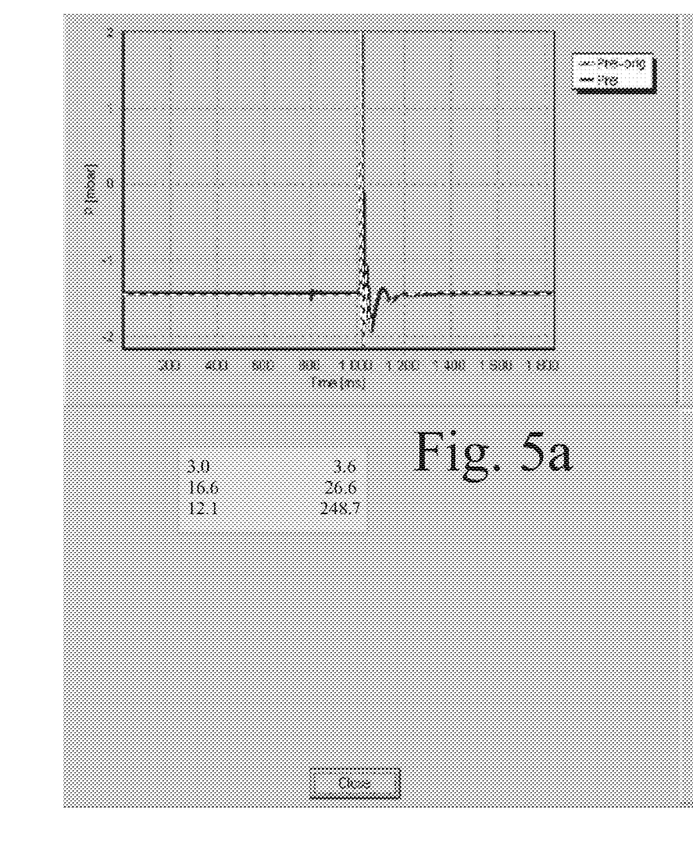
FIGS. 5a-5c show graphically the operation of the invention, in such a way that, in the sorbent-filled 2nd sorbent channel a high reading value can also be seen in the lower left-hand FIG. 5c (12.1 and 248.7). Changes can also be detected in the $1^{st}$ sorbent channel.
Figure 5B:
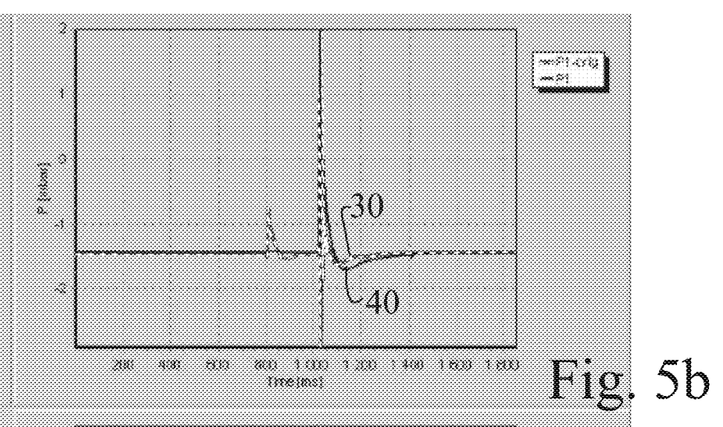
Figure 5C:
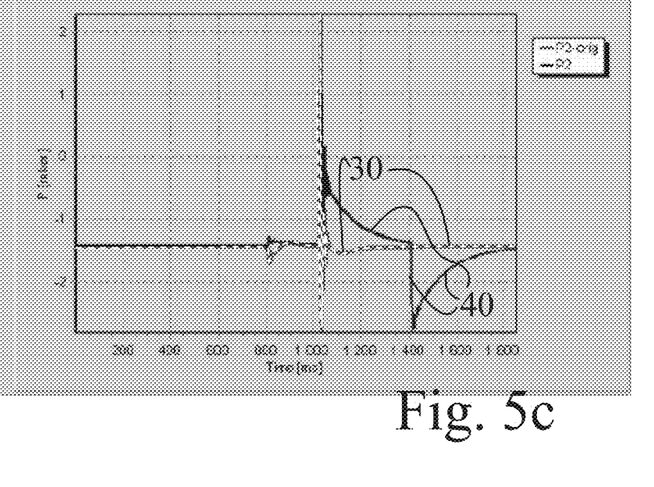

It can be seen from the curve of FIG. 5c that sorbent has been filled in the 2$^{nd}$ sorbent channel, which also appears as a high reading value at the lower left (12.1 and 248.7). Changes can also be detected in the 1$^{st}$ sorbent channel on the basis of FIG. 5b, whereas FIG. 5a represents a situation that is under the limit values.

Figure 6A:
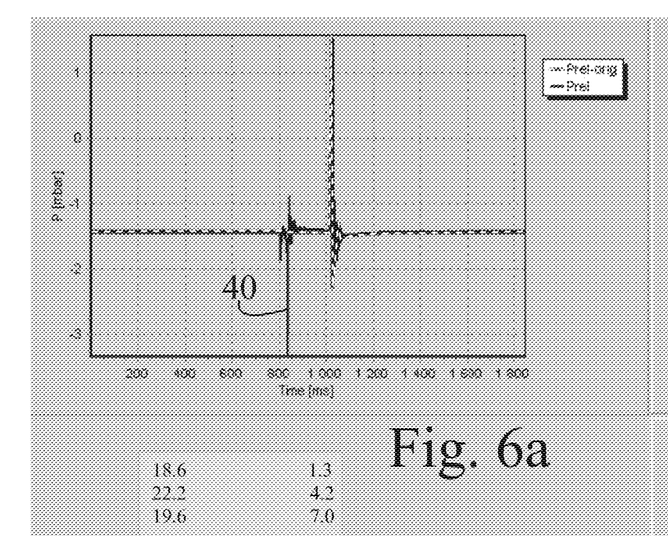
FIGS. 6a-6c show graphically the operation of the invention, in such a way that the left-hand FIG. 6a demonstrates that there is a blockage in the sample-gas suction piping. The effect of the blockage is also visible in the right-hand pressure curves in FIGS. 6b and 6c. The reading values have increased to >10.
Figure 6B:
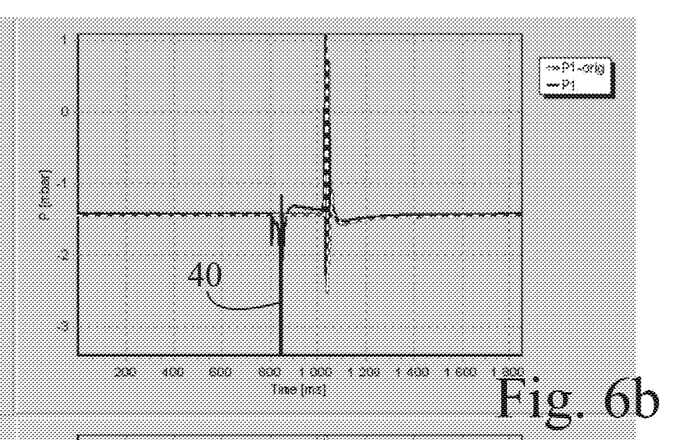
Figure 6C:
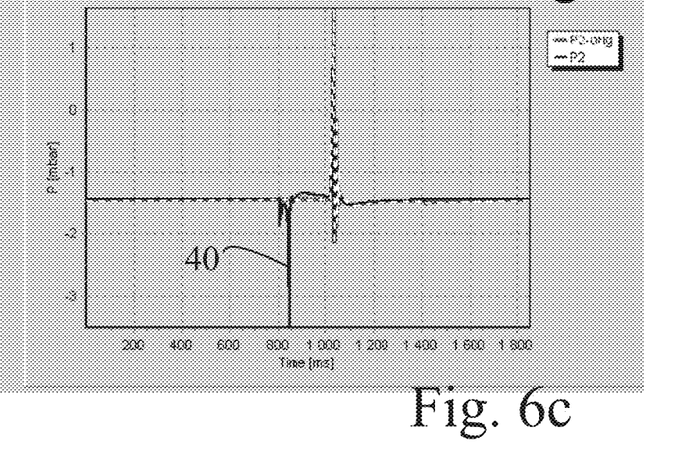

A blockage in the sample-gas suction piping can be seen from the curve of FIG. 6a. The effect of the blockage can also be seen in the right-hand pressure curves in FIGS. 6b and 6c. In all of the figures, the values of the second reading value pairs have increased above the limit value 10.

FIGS. 3a-6c show the pressure pulses of the pump's cycle as a function of time. The blockage of the suction side is detected in front of the actual work pulse, i.e. in the time preceding the pulse.

The following explains the matter:

The pumping cycle is formed on the following principle, with reference to FIG. 2:

A. Suction valve 4 open.
B. Pump membrane of pump 5 to the upper position.
C. Suction valve 4 closed.
D. Outlet valve 6 open.
E. Pump membrane of pump 5 to the lower position, when the visible pulse is created.
D. Outlet valve 6 closed.

A pressure sensor 8 or microphone is located after the outlet valve 6.

From this cycle, it can be seen that the pressure pulse is always directed in normal operation to the piping on the outlet side of pump 5. According to the programming, the pulse is directed to the outlet or to the collection of some specific sample.

From each of these, the back-reflected pressure shock can be seen in the time after the work pulse.

In this case, the so-called echosounding is operating normally. However, the outlet valve of pump 5 closes before the arriving echo and the slow pressure drop of the work pulse caused by the blockage is sufficient indication of the events.

The phenomena of the time before the work pulse are in the time when the pump's inlet valve opens. The outlet valve is then closed and the possible blockage in front of the pump has created a vacuum in the inlet line during the previous cycles.

This vacuum transfers to the interior parts of the pump and when the outlet valve opens this vacuum pulse is seen in the pressure sensor. The pump's internal volume fills through the outlet-side channels.

This chain of events shows a blockage in the devices on the suction side of the pump 5, but does not exploit the back-reflection information.

A pressure pulse oriented in the desired direction can be easily attached to an environmental analysis of pump 5.

By monitoring the back reflections, information can be obtained by means of the same device on the magnitude of the change, and, on the basis of the arrival time of the reflection, on the distance of that change relative to the pump.

In the present application, the term measurement piping typically refers to the piping connecting the pump 4, 5, 6 and the collection sorbents 12, 13, including the collection sorbents 12, 13 and the other components, such as valves. The measurement piping can also include other parts of the measurement system, such as the gas inlet channel 21 nd the gas outlet channel 22.

In the present application, the term modelling refer to the creation of a computational model on the basis of measurement.

The invention claimed is:

1. A sampling method comprising the steps of: leading a sample through an inlet channel to a pump and from there on to sampling means through measurement piping, producing, via the pump, a pressure pulse in the measurement piping, measuring an echo of the pressure pulse in the measurement piping and estimating the change of the echoes caused by the pressure pulse as a function of time in order to determine the condition of the measurement piping, wherein the inlet channel is a flow-line and the pump is formed of a pump and magnetic valves located on either side of the pump, and further comprising the step of controlling the magnetic valves in such a way that the pumping is pulse-like.

2. A sampling method according to claim 1, further comprising the steps of forming a pumping pulse from the following sequence:
   A. opening a suction valve, wherein the suction valve is one of the magnetic valves,
   B. moving the actual pump's pump membrane to the upper position,
   C. closing the suction valve,
   D. opening an outlet valve, wherein the outlet valve is the other of the magnetic valves,
   E. moving the actual pump's pump membrane to the upper position when a visible pulse is created, and
   D. closing the outlet valve.

3. A sampling method according to claim 1 wherein the pressure pulse is measured after the pump in the flow direction as a function of time in order to create an impulse response in the piping of the measuring device.

4. A sampling method according to claim 1, further comprising the steps of:
   creating a reference value at the beginning of the measurement, when the measurement piping is clean, in order to create an impulse response in the measuring device's measurement piping), and
   repeatedly evaluating the impulse response at the moment of measurement against the reference impulse response, in order to assess the condition of the measurement piping and the sample collectors.

5. A sampling method according to claim 1, wherein a pressure pulse is produced by at least one of a control element and a valve in a desired direction in the measurement piping, when assessing the condition of the measurement piping.

6. A sampling method according to claim 1, wherein at least one three-way valve is used to direct a flow to different sampling elements.

7. A sampling method according to claim 1, wherein the pump is operated on a blow-back principle.

8. A pressure-measurement method comprising the steps of; leading a sample through an inlet channel to a pump and from there on to sampling means through measurement piping, producing a pressure pulse in the measurement piping, measuring an echo of the pressure pulse in the measurement piping, estimating the change of the echoes caused by the pressure pulse as a function of time in order to determine the condition of the measurement piping, measuring the pressure in a set of inlet channels containing a liquid or a gas, repeatedly measuring an impulse-response of the pressure in the set of inlet channels, and on the basis of the measured impulse-response information, modelling the pressure of the entire set of channels.

9. A sampling apparatus comprising:
   measurement piping, which has at least a flowline,
   a pump connected to the flowline, wherein the pump is capable of producing a pressure pulse in the measurement piping
   a sampling means connected to the pump by the measurement piping for taking a sample from the flow, and
   a means for measuring an echo of a pressure pulse produced by the pump and for evaluating changes in the shape of the echoes caused by the pressure pulse, as a function of time, in order to determine the condition of the measurement piping.

10. A sampling apparatus according to claim 9, wherein the pump has a pump and magnetic valves located on either side of it, and
   wherein the sampling apparatus further comprises control elements for controlling the pump and the valves in such a way that pumping is pulse-like.

11. A sampling apparatus according claim 10, wherein the control elements have means for determining an impulse response of the pulse-like pumping pulse at different moments in time and for comparing the impulse responses determined at different moments in time with each other.

12. A sampling apparatus according to claim 9, further comprising a pressure-measurement device which is located after the pump in a designated flow direction.

13. A sampling apparatus according to claim 9, further comprising at least one three-way valve for directing the flow to various sampling elements.

* * * * *